US009108967B2

(12) United States Patent
Hudlicky et al.

(10) Patent No.: US 9,108,967 B2
(45) Date of Patent: Aug. 18, 2015

(54) PROCESS FOR THE PREPARATION OF MORPHINE ANALOGS VIA METAL CATALYZED N-DEMETHYLATION/FUNCTIONALIZATION AND INTRAMOLECULAR GROUP TRANSFER

(71) Applicant: Brock University, St. Catharines, Ontario (CA)

(72) Inventors: Tomas Hudlicky, St. Catharines (CA); Ales Machara, Brevnov (CZ)

(73) Assignee: Brock University, St. Catharines, Ontario (CA)

( * ) Notice: Subject to any disclaimer, the term of this patent is extended or adjusted under 35 U.S.C. 154(b) by 0 days.

(21) Appl. No.: 14/571,714

(22) Filed: Dec. 16, 2014

(65) Prior Publication Data

US 2015/0094471 A1 Apr. 2, 2015

Related U.S. Application Data

(62) Division of application No. 13/464,247, filed on May 4, 2012, now Pat. No. 8,946,214.

(60) Provisional application No. 61/483,264, filed on May 6, 2011.

(51) Int. Cl.
*A61K 31/535* (2006.01)
*C07D 489/02* (2006.01)

(52) U.S. Cl.
CPC ................... *C07D 489/02* (2013.01)

(58) Field of Classification Search
CPC ..................................................... C07D 489/08
USPC ...................................................... 514/232.2
See application file for complete search history.

(56) References Cited

U.S. PATENT DOCUMENTS

| | | | |
|---|---|---|---|
| 4,161,597 | A | 7/1979 | Olofson et al. |
| 4,472,253 | A | 9/1984 | Schwartz |
| 4,613,668 | A | 9/1986 | Rice |
| 5,668,285 | A | 9/1997 | Rice et al. |
| 6,399,078 | B1 | 6/2002 | Devico et al. |
| 6,440,688 | B1 | 8/2002 | Bruce et al. |
| 7,405,301 | B2 | 7/2008 | Scammells et al. |
| 7,935,820 | B2 | 5/2011 | Carroll et al. |
| 7,999,104 | B2 | 8/2011 | Carroll et al. |
| 8,946,214 | B2 | 2/2015 | Hudlicky et al. |
| 2009/0005565 | A1 | 1/2009 | Carroll et al. |
| 2009/0156820 | A1 | 6/2009 | Wang et al. |
| 2011/0313163 | A1 | 12/2011 | Hudlicky et al. |

FOREIGN PATENT DOCUMENTS

| | | |
|---|---|---|
| CA | 913077 | 10/1972 |
| CN | 101955484 A1 | 1/2011 |
| EP | 0 164 290 A1 | 12/1985 |
| FR | 2395269 | 1/1979 |
| GB | 975601 | 11/1964 |
| GB | 2000137 A | 1/1979 |
| WO | 98/05667 | 2/1998 |
| WO | 01/34608 | 5/2001 |
| WO | 2005/047291 | 5/2005 |
| WO | 2005/113557 | 12/2005 |
| WO | 2006/104656 | 10/2006 |
| WO | 2010/121369 A1 | 10/2010 |

OTHER PUBLICATIONS

Isao Seki Takamine Kenkyusho Nenpo 1960, 12, 56-62—English translation.*
Ripper, Justin A., "Photochemical N-Demethylation of Alkaloids", Bioorganic & Medicinal Chemistry Letters 11 (2001), pp. 443-445.
Carroll, R.J., et al., "Palladium-Catalyzed N-Demethylation/N-Acylation of Some Morphine and Tropane Alkaloids", Adv. Synth. Catal. 2008, 350: 2584.
Sugi, Yoshihiro et al., "Dealkylation of N,N-dialkylanilines over transition metal catalysts in the presence of ammonia, water and hydrogen", Applied Catalysis A.: General, 103 (1993), 43-53.
Guo, Yukun, et al., "Kinetics and mechanism of oxidation of n-methylethylamine by bis(hydrogenperiodato)argentate (III) complex anion", Transition Met Chem (2011), 36:56-64.
Kok, G., et al. "An improved process for the N-demethylation of opiate alkaloids using an Iron(II) Catalyst in Acetate Buffer." Adv. Synth. Catal. 2009, 351:283-286.
Dong, Z. et al. "New methodology for the N-demethylation of opiate alkaloids." J. Org. Chem. 2007, 72:9881-9885.
Kok, G.B., et al. "N-demethylation of N-methyl alkaloids with ferrocene." Bioorg. Med. Chem. Lett. 2010, 20:4499-4502.
International Search Report and Written Opinion of PCT/CA2012/000424 dated Aug. 23, 2012.
Iijima, I., et al., "Studies in the (+) Morphinan series I. An alternate conversion of (+)-dihydrocodeinone into (+)-codeine." Heterocycles, 1997; 6:1157-1165.
Seki, Isao, Takamine Kengyusho Nenpo, 12: 56-62 (1960).
Partial supplementary European search report, dated Nov. 13, 2014, issued in corresponding European Patent Application No. 12782542.0.
Evsikova, I.V. et al., "Carbonate derivatives of 14B-hydroxycodeine", Russian Chemical Bulletin, International Edition, 57(8): 1773-1774 (2008).
Hosztafi, Sandor et al., "Morphine Alkaloids, Part 114, A Stereohomogeneous Synthesis of N-Demethyl-N-Substituted-14-Hydroxydihydromorphines".
Schmidhammer, Helmut et al., "5-Methylnaloxone and 5-Methylnaltrexone: Synthesis and Pharmacological Evaluation", Helvetica Chimica Acta, 73: 1986-1990 (1990).
Schwartz, Martin A. et al., "Efficient Synthesis of 14-Hydroxymorphinans from Codeine", Journal of Medicinal Chemistry, 24(12): 1525-1528 (1981).
Toth, Geza et al., "Tritium Labelling of Naltrindole, a o-Receptor-Selective Opioid Antagonist via 1-Bromonaltrexone", Helvetica Chimica Acta, 76: 2274-2278 (1993).
Extended European Search Report, dated Feb. 10, 2015, issued in correspondence European Patent Application No. 12782542.0.

\* cited by examiner

*Primary Examiner* — John Mabry

(74) *Attorney, Agent, or Firm* — Patrick J. Hagan; Dann, Dofman, Herrell and Skillman, P.C.

(57) ABSTRACT

The present application is directed to an efficient conversion of C-14 hydroxylated morphine alkaloids to various morphine analogs, such as naltrexone, naloxone and nalbuphone. One feature of this process is an intramolecular functional group transfer from the C-14 hydroxyl to the N-17 nitrogen atom following a palladium-catalyzed N-demethylation.

16 Claims, No Drawings

PROCESS FOR THE PREPARATION OF MORPHINE ANALOGS VIA METAL CATALYZED N-DEMETHYLATION/FUNCTIONALIZATION AND INTRAMOLECULAR GROUP TRANSFER

CROSS-REFERENCE TO RELATED APPLICATIONS

The present application is a divisional patent application of co-pending patent application Ser. No. 13/464,247 filed on May 4, 2012 which claims the benefit of priority from U.S. provisional application No. 61/483,264 filed on May 6, 2011, the contents of both of which are incorporated herein by reference in their entirety.

FIELD OF THE APPLICATION

The present application relates to an efficient N-demethylation/functionalization/reduction sequence for C-14 hydroxylated morphine alkaloids such as, oxymorphone, in particular for the preparation of various morphine analogs such as naltrexone, naloxone and nalbuphone.

BACKGROUND OF THE APPLICATION

The synthesis of all opiate-derived analgesic agents as well as the various antagonists or mixed agonists currently used in medicine originates in naturally occurring alkaloids isolated from the opium poppy latex. The most commonly used are morphine and its congeners codeine, thebaine, and oripavine, shown in Scheme 1.

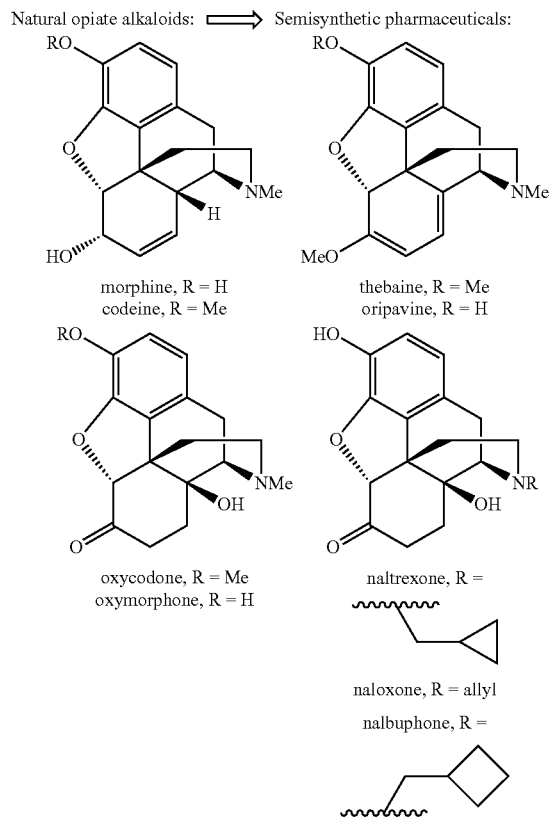

There are two major challenges in the large scale manufacture of the ubiquitously used pharmaceutical agents such as oxycodone, oxymorphone, naltrexone, naloxone, and nalbuphone, also shown in Scheme 1.

The first of the two challenges, the introduction of the C-14 hydroxyl represents an important step in the manufacture of all of these compounds. Nevertheless, this problem has been adequately solved by various oxidation protocols and thebaine and oripavine lend themselves as especially convenient starting materials for the C-14 hydroxylated analogs. Thus one would not expect that much improvement could be incorporated into the manufacturing process save for completely new methods involving C—H activation or biological catalysis. The second challenge, and a much more difficult one, rests in the formal exchange of the N-methyl group of natural opiates for the N-cyclopropylmethyl, N-allyl, or N-cyclobutylmethyl functionality found in naltrexone, naloxone, and nalbuphone, respectively.

The N-demethylation protocols previously reported include the von Braun reaction employing cyanogen bromide[i], chloroformate reagents[ii], photochemical methods[iii], demethylation of N-oxides[iv], as well as microbial[v] and enzymatic[vi] methods. The secondary amines are then converted to the corresponding products by alkylation. N-Demethylation/acylation of hydrocodone and tropane alkaloids was also accomplished via palladium catalysts that provided N-acetylhydrocodone and other acyl derivatives.[vii]

SUMMARY OF THE APPLICATION

As it appears likely that the synthesis of oxymorphone from oripavine or thebaine proceeds efficiently on industrial scale, the present application relates to the efficient conversion of C-14 hydroxy morphone alkaloids, such as oxymorphone, to various morphine analogs, such as naltrexone, naloxone and nalbuphone, in a direct way. For example, oxymorphone was transformed in three chemical steps and 75% overall yield to naltrexone. The features of this process involve intramolecular acyl transfer from the C-14 hydroxyl to the nitrogen atom following metal-catalyzed N-demethylation. In one embodiment of the process, the cyclopropylcarboxamide was then reduced, along with the ester protecting groups at C-3 and C-6.

Accordingly, the present application includes a process for the preparation of a compound of Formula I:

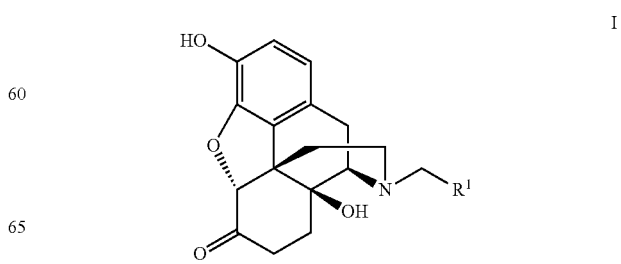

the process comprising:

(a) reacting a compound of Formula II with a compound of Formula IIIa or IIIb under conditions to provide a compound of Formula IV:

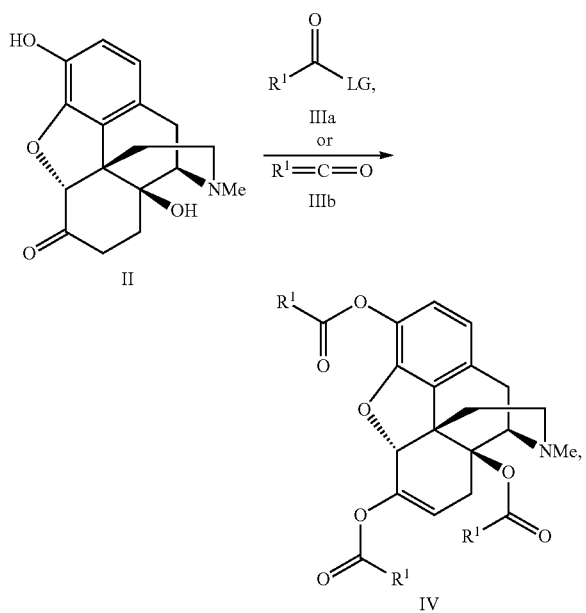

(b) reacting the compound of Formula IV with a metal catalyst in the presence of an oxidant under conditions to provide a compound of Formula V:

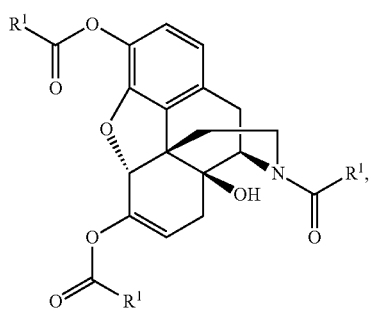

and (c) treating the compound of Formula V with a reducing agent under conditions to provide the compound of Formula I, wherein each $R^1$ is selected from $C_{3-10}$cycloalkyl, $C_{1-10}$alkyl, and $C_{6-10}$aryl, and LG is a leaving group; and wherein in the compounds of the Formulae I, III, IV and V, one or more available hydrogens in $R^1$ is/are optionally replaced with F and/or one or more of available atoms in $R^1$ is/are optionally replaced with an isotopic label.

The process of the present application can also include the transfer of other functional groups from the C-14 hydroxyl group to N-17 on other morphine analogs. Therefore, the present application also includes a process for the preparation of a compound of Formula VI:

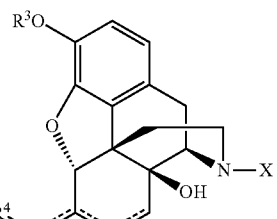

wherein
X is selected from $C(O)R^2$, $S(O)R^2$, $SO_2R^2$, $P(O)R^2R^{2'}$, $P(O)(OR^2)R^{2'}$ and $P(O)(OR^2)(OR^{2'})$;
$R^2$ and $R^{2'}$ are independently selected from $C_{3-10}$cycloalkyl, $C_{3-10}$heterocycloalkyl, $C_{3-10}$cycloalkenyl, $C_{1-10}$alkyl, $C_{2-10}$alkenyl, $C_{6-10}$aryl and $C_{5-10}$heteroaryl, each of the latter groups being unsubstituted or substituted with one or more substituents independently selected from $C_{1-4}$alkyl, $OC_{1-4}$alkyl, halo, CN, $NO_2$, $C_{6-10}$aryl and $OC_{6-10}$aryl;
⸺ represents a single or double bond, provided that two double bonds are not adjacent to each other; and
$R^3$ and $R^4$ are independently selected from $C_{1-10}$alkyl, $C_{6-10}$aryl, $C_{3-10}$cycloalkyl, $C_{1-10}$alkylene$C_{6-10}$aryl, $C_{1-10}$alkylene$C_{3-10}$cycloalkyl and PG, except when ⸺ represents =O, then $R^4$ is not present;
the process comprising:
(a) reacting a compound of Formula VII with a compound of Formula VIII(a) or VIII(b) under conditions to provide a compound of Formula IX:

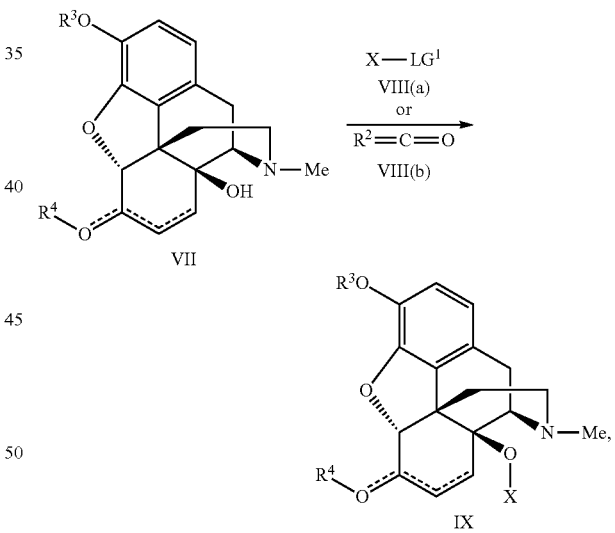

wherein $LG^1$ is a leaving group;
X is selected from $C(O)R^2$, $S(O)R^2$, $SO_2R^2$, $P(O)R^2R^{2'}$, $P(O)(OR^2)R^{2'}$ and $P(O)(OR^2)(OR^{2'})$;
$R^2$ and $R^{2'}$ are independently selected from $C_{3-10}$cycloalkyl, $C_{3-10}$heterocycloalkyl, $C_{3-10}$cycloalkenyl, $C_{1-10}$alkyl, $C_{2-10}$alkenyl, $C_{6-10}$aryl and $C_{5-10}$heteroaryl, each of the latter groups being unsubstituted or substituted with one or more substituents independently selected from $C_{1-4}$alkyl, $OC_{1-4}$alkyl, halo, CN, $NO_2$, $C_{6-10}$aryl and $OC_{6-10}$aryl;
⸺ represents a single or double bond, provided that two double bonds are not adjacent to each other; and
$R^3$ and $R^4$ are independently selected from $C_{1-10}$alkyl, $C_{6-10}$aryl, $C_{3-10}$cycloalkyl, $C_{1-10}$alkylene$C_{6-10}$aryl, $C_{1-10}$alkylene$C_{3-10}$cycloalkyl and PG, except when ≕ represents =O, then $R^4$ is not present; and (b) reacting the compound of Formula IX with a metal catalyst in the presence of an oxidant under conditions to provide the compound of Formula VI, wherein in the compounds of Formulae VI, VII, VIII and IX, one or more available hydrogens in $R^2$, $R^{2'}$, $R^3$ and $R^4$ is/are optionally replaced with F and/or one or more of available atoms in $R^2$, $R^{2'}$, $R^3$ and $R^4$ is/are optionally replaced with an isotopic label.

In an embodiment, the compound of Formula VI is selected from a compound of Formula VI(a), VI(b) and VI(c):

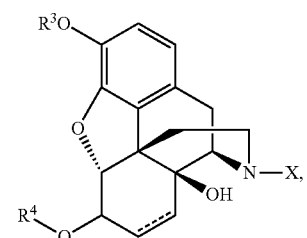

VI(a)

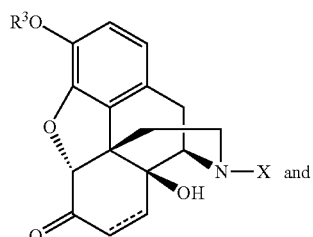

VI(b)

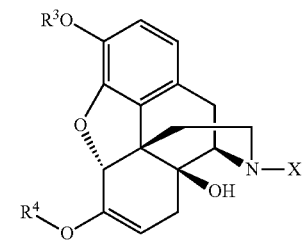

VI(c)

wherein
X is selected from $C(O)R^2$, $S(O)R^2$, $SO_2R^2$, $P(O)R^2R^{2'}$, $P(O)(OR^2)R^{2'}$ and $P(O)(OR^2)(OR^{2'})$;

$R^2$ and $R^{2'}$ are independently selected from $C_{3-10}$cycloalkyl, $C_{3-10}$heterocycloalkyl, $C_{3-10}$cycloalkenyl, $C_{1-10}$alkyl, $C_{2-10}$alkenyl, $C_{6-10}$aryl and $C_{5-10}$heteroaryl, each of the latter groups being unsubstituted or substituted with one or more substituents independently selected from $C_{1-4}$alkyl, $OC_{1-4}$alkyl, halo, CN, $NO_2$, $C_{6-10}$aryl and $OC_{6-10}$aryl;

≕ represents a single or double bond;

$R^3$ and $R^4$ are independently selected from $C_{1-10}$alkyl, $C_{6-10}$aryl, $C_{3-10}$cycloalkyl, $C_{1-10}$alkylene$C_{6-10}$aryl, $C_{1-10}$alkylene$C_{3-10}$cycloalkyl and PG, and one or more available hydrogens in $R^2$, $R^{2'}$, $R^3$ and $R^4$ is/are optionally replaced with F and/or one or more of available atoms in $R^2$, $R^{2'}$, $R^3$ and $R^4$ is/are optionally replaced with an isotopic label.

The compounds of Formula VI are useful intermediates in the preparation of morphine alkaloids. For example, in one embodiment, the X group may be selectively removed, via acid or base hydrolysis, from N-17, to provide the corresponding secondary amine of Formula X:

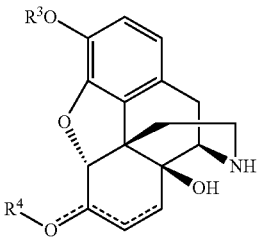

X wherein
≕ represents a single or double bond, provided that two double bonds are not adjacent to each other;
$R^3$ and $R^4$ are independently selected from $C_{1-10}$alkyl, $C_{6-10}$aryl, $C_{3-10}$cycloalkyl, $C_{1-10}$alkylene$C_{6-10}$aryl, $C_{1-10}$alkylene$C_{3-10}$cycloalkyl and PG, except when ≕ represents =O, then $R^4$ is not present; and one or more available hydrogens in $R^3$ and $R^4$ is/are optionally replaced with F and/or one or more of available atoms in $R^3$ and $R^4$ is/are optionally replaced with an isotopic label. The N-17 secondary amine may then be selectively alkylated with any number of alkylating reagents to provide a variety of substituents at this position. The process is particularly useful for exploring the structure activity relationship of different groups at this location. In an embodiment, the N-17 secondary amine of the compound of Formula X is selectively alkylated with a cyclopropylmethyl, cyclobutylmethyl or allyl group.

In another embodiment, compounds of Formula VI(a), VI(b) or VI(c) wherein X is "—$C(O)R^2$" may be reduced, to provide the corresponding compound of Formula XI(a), XI(b) or XI(c), respectively:

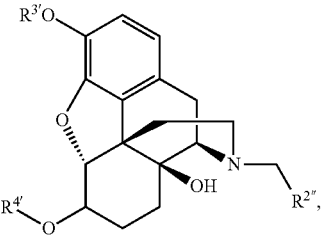

XI(a)

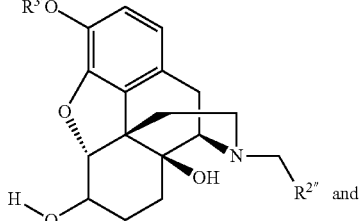

XI(b)

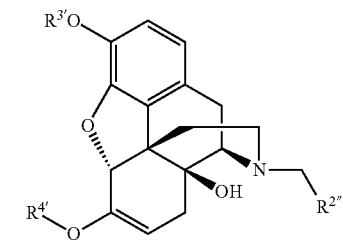

XI(c)

wherein
$R^{2''}$ is selected from $C_{3-10}$cycloalkyl, $C_{3-10}$heterocycloalkyl, $C_{1-10}$alkyl, $C_{6-10}$aryl and $C_{5-10}$heteroaryl, each of the latter groups being unsubstituted or substituted with one or more substituents independently selected from $C_{1-4}$alkyl, $OC_{1-4}$alkyl, halo, CN, $NO_2$, $C_{6-10}$aryl and $OC_{6-10}$aryl;

$R^{3'}$ and $R^{4'}$ are independently selected from $C_{1-10}$alkyl, $C_{6-10}$aryl, $C_{3-10}$cycloalkyl, $C_{1-10}$alkylene$C_{6-10}$aryl, $C_{1-10}$alkylene$C_{3-10}$cycloalkyl and PG; and one or more available hydrogens in $R^{2''}$, $R^{3'}$ and $R^{4'}$ is/are optionally replaced with F and/or one or more of available atoms in $R^{2''}$, $R^{3'}$ and $R^{4'}$ is/are optionally replaced with an isotopic label, wherein when PG is a protecting group that is removed by the reducing agent, $R^{3'}$ and $R^{4'}$ are H and the compound of Formula XI(c) converts to the ketone form.

The present application also includes compounds of Formula IV and V, useful for the preparation of compounds of Formula I.

Other features and advantages of the present application will become apparent from the following detailed description. It should be understood, however, that the detailed description and the specific examples while indicating embodiments of the application are given by way of illustration only, since various changes and modifications within the spirit and scope of the application will become apparent to those skilled in the art from this detailed description.

DETAILED DESCRIPTION OF THE APPLICATION

I. Definitions

Unless otherwise indicated, the definitions and embodiments described in this and other sections are intended to be applicable to all embodiments and aspects of the application herein described for which they are suitable as would be understood by a person skilled in the art.

As used in this application, the singular forms "a", "an" and "the" include plural references unless the content clearly dictates otherwise. For example, an embodiment including "a reducing agent" should be understood to present certain aspects with one reducing agent, or two or more additional compounds.

In embodiments comprising an "additional" or "second" component, such as an additional or second reducing agent, the second component as used herein is chemically different from the other components or first component. A "third" component is different from the other, first, and second components, and further enumerated or "additional" components are similarly different.

The term "suitable" as used herein means that the selection of the particular compound or conditions would depend on the specific synthetic manipulation to be performed, and the identity of the molecule(s) to be transformed, but the selection would be well within the skill of a person trained in the art. All process/method steps described herein are to be conducted under conditions sufficient to provide the product shown. A person skilled in the art would understand that all reaction conditions, including, for example, reaction solvent, reaction time, reaction temperature, reaction pressure, reactant ratio and whether or not the reaction should be performed under an anhydrous or inert atmosphere, can be varied to optimize the yield of the desired product and it is within their skill to do so.

In embodiments of the application, the compounds described herein have at least one asymmetric centre. Where compounds possess more than one asymmetric centre, they may exist as diastereomers. It is to be understood that all such isomers and mixtures thereof in any proportion are encompassed within the scope of the present application. It is to be further understood that while the stereochemistry of the compounds may be as shown in any given compound listed herein, such compounds may also contain certain amounts (e.g. less than 20%, suitably less than 10%, more suitably less than 5%) of compounds of the application having alternate stereochemistry.

In understanding the scope of the present disclosure, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. The term "consisting" and its derivatives, as used herein, are intended to be closed terms that specify the presence of the stated features, elements, components, groups, integers, and/or steps, but exclude the presence of other unstated features, elements, components, groups, integers and/or steps. The term "consisting essentially of", as used herein, is intended to specify the presence of the stated features, elements, components, groups, integers, and/or steps as well as those that do not materially affect the basic and novel characteristic(s) of features, elements, components, groups, integers, and/or steps.

Terms of degree such as "substantially", "about" and "approximately" as used herein mean a reasonable amount of deviation of the modified term such that the end result is not significantly changed. These terms of degree should be construed as including a deviation of at least ±5% of the modified term if this deviation would not negate the meaning of the word it modifies.

The term "alkyl" as used herein, whether it is used alone or as part of another group, means straight or branched chain, saturated alkyl groups. The term $C_{1-6}$alkyl means an alkyl group having 1, 2, 3, 4, 5, or 6 carbon atoms. It is an embodiment of the application that, in the alkyl groups, one or more, including all, of the hydrogen atoms are optionally replaced with F or $^2H$ and thus include, for example trifluoromethyl, pentafluoroethyl and the like.

The term "alkylene" as used herein, whether alone or as part of another group, means an alkyl group that is bivalent; i.e. that is substituted on two ends with another group. The term $C_{1-10}$alkylene means an alkylene group having 1, 2, 3, 4, 5, 6, 7, 8, 9 or 10 carbon atoms. It is an embodiment of the application that, in the alkylene groups, one or more, including all, of the hydrogen atoms are optionally replaced with F or $^2H$.

The term "alkenyl" as used herein, whether it is used alone or as part of another group, means straight or branched chain, unsaturated alkenyl groups. The term $C_{2-6}$alkenyl means an alkenyl group having 2, 3, 4, 5, or 6 carbon atoms and at least one double bond. It is an embodiment of the application that, in the alkenyl groups, one or more, including all, of the hydrogen atoms are optionally replaced with F or $^2H$ and thus include, for example trifluoroethenyl, pentafluoropropenyl and the like.

The term "cycloalkyl" as used herein, whether it is used alone or as part of another group, means cyclic, saturated alkyl groups. The term $C_{3-10}$cycloalkyl means a cycloalkyl group having 3, 4, 5, 6, 7, 8, 9 or 10 carbon atoms. It is an embodiment of the application that, in the cycloalkyl groups, one or more, including all, of the hydrogen atoms are optionally replaced with F or $^2H$.

The term "cycloalkenyl" as used herein, whether it is used alone or as part of another group, means cyclic, unsaturated alkyl groups. The term $C_{3-10}$cycloalkenyl means a cycloalkenyl group having 3, 4, 5, 6, 7, 8, 9 or 10 carbon atoms and at least one double bond. It is an embodiment of the application that, in the cycloalkenyl groups, one or more, including all, of the hydrogen atoms are optionally replaced with F or $^2$H.

The term "heterocycloalkyl" as used herein, whether it is used alone or as part of another group, means cyclic, saturated alkyl groups containing at least one heteroatom, such as N, O, and/or S. The term $C_{3-10}$heterocycloalkyl means a heterocycloalkyl group having 3, 4, 5, 6, 7, 8, 9 or 10 carbon atoms, in which at least one of the carbon atoms has been replaced with a heteroatom, such as N, O and/or S. It is an embodiment of the application that, in the heterocycloalkyl groups, one or more, including all, of the hydrogen atoms are optionally replaced with F or $^2$H.

The term "aryl" as used herein refers to cyclic groups that contain at least one aromatic ring. In an embodiment of the application, the aryl group contains 6, 9 or 10 atoms, such as phenyl, naphthyl or indanyl. It is an embodiment of the application that, in the aryl groups, one or more, including all, of the hydrogen atoms are optionally replaced with F or $^2$H and thus include, for example pentafluorophenyl and the like.

The term "heteroaryl" as used herein refers to cyclic groups that contain at least one aromatic ring and at least one heteroatom, such as N, O and/or S. The term $C_{5-10}$heteroaryl means an aryl group having 5, 6, 7, 8, 9 or 10 atoms, in which at least one atom is a heteroatom, such as N, O and/or S. It is an embodiment of the application that, in the heteroaryl groups, one or more, including all, of the hydrogen atoms are optionally replaced with F or $^2$H and thus include, for example tetrafluoropyridyl and the like.

The term "reducing agent" as used herein means any compound or combination of compounds that reduces a desired functional group. A reducing agent results in the overall addition of electrons, or in the case of organic chemistry, hydrogen atoms to the functional group.

The term "oxidant" as used herein refers to a reagent that provides an oxygen species for participation in the metal catalyzed reactions of the present application. In an embodiment, the oxygen source is $O_2$ gas, air or an inorganic or organic peroxide (i.e. a compound comprising an "O—O" functionality).

The term "inert solvent" as used herein means a solvent that does not interfere with or otherwise inhibit a reaction. Accordingly, the identity of the inert solvent will vary depending on the reaction being performed. The selection of inert solvent is within the skill of a person in the art. Examples of inert solvents include, but are not limited to, benzene, toluene, tetrahydrofuran, ethyl ether, ethyl acetate, dimethyl formamide (DMF), acetonitrile, $C_{1-6}$alkylOH (e.g. methanol, ethanol, n-propanol, 2-propanol, n-butanol, butan-2-ol and 2-methyl-1-propanol), diethylcarbonate, hexane and dimethylslfoxide (DMSO). Further examples, can include aqueous solutions, such as water and dilute acids and bases, and ionic liquids, provided that such solvents do not interfere with the reaction.

The term "solvent" includes both a single solvent and a mixture comprising two or more solvents.

The term "available", as in "available hydrogen atoms" or "available atoms" refers to atoms that would be known to a person skilled in the art to be capable of replacement by either a fluorine atom (in the case of hydrogen atoms) or isotopic labels (in the case of all atoms) using methods known in the art.

The term "halo" as used herein refers to a halogen atom and includes F, Cl, Br and I.

t-Boc as used herein refers to the group t-butyloxycarbonyl.

Ac as used herein refers to the group acetyl.

Ts (tosyl) as used herein refers to the group p-toluenesulfonyl

Ms as used herein refers to the group methanesulfonyl

TBDMS as used herein refers to the group t-butyldimethylsilyl.

TBDPS as used herein refers to the group t-butyldiphenylsilyl.

TMS as used herein refers to the group trimethylsilyl.

Tf as used herein refers to the group trifluoromethanesulfonyl.

Ns as used herein refers to the group naphthalene sulphonyl.

Bn as used herein refers to the group benzyl.

Fmoc as used herein refers to the group fluorenylmethoxycarbonyl.

The term "leaving group" or "LG" as used herein refers to a group that is readily displaceable by a nucleophile, for example, under nucleophilic substitution reaction conditions. Examples of suitable leaving groups include, but are not limited to, halo, Ms, Ts, Ns, Tf, $C_{1-6}$acyl, and the like.

The terms "protective group" or "protecting group" or "PG" or the like as used herein refer to a chemical moiety which protects or masks a reactive portion of a molecule to prevent side reactions in those reactive portions of the molecule, while manipulating or reacting a different portion of the molecule. After the manipulation or reaction is complete, the protecting group is removed under conditions that do not degrade or decompose the remaining portions of the molecule. The selection of a suitable protecting group can be made by a person skilled in the art. Many conventional protecting groups are known in the art, for example as described in "Protective Groups in Organic Chemistry" McOmie, J. F. W. Ed., Plenum Press, 1973, in Greene, T. W. and Wuts, P. G. M., "Protective Groups in Organic Synthesis", John Wiley & Sons, 3$^{rd}$ Edition, 1999 and in Kocienski, P. Protecting Groups, 3rd Edition, 2003, Georg Thieme Verlag (The Americas). Examples of suitable protecting groups include, but are not limited to t-Boc, Ac, Ts, Ms, silyl ethers such as TMS, TBDMS, TBDPS, Tf, Ns, Bn, Fmoc, dimethoxytrityl, methoxyethoxymethyl ether, methoxymethyl ether, pivaloyl, p-methyoxybenzyl ether, tetrahydropyranyl, trityl, ethoxyethyl ethers, carbobenzyloxy, benzoyl and the like.

The expression "proceed to a sufficient extent" as used herein with reference to the reactions or process steps disclosed herein means that the reactions or process steps proceed to an extent that conversion of the starting material or substrate to product is maximized. Conversion may be maximized when greater than about 5, 10, 15, 20, 25, 30, 35, 40, 45, 50, 55, 60, 65, 70, 75, 80, 85, 90, 95 or 100% of the starting material or substrate is converted to product.

II. Methods of the Application

The present application includes a process for the preparation of a compound of Formula I:

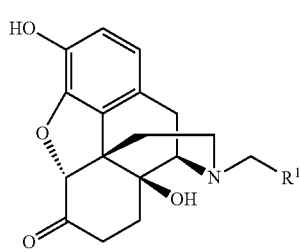

comprising:
(a) reacting a compound of Formula II with a compound of Formula IIIa or IIIb under conditions to provide a compound of Formula IV:

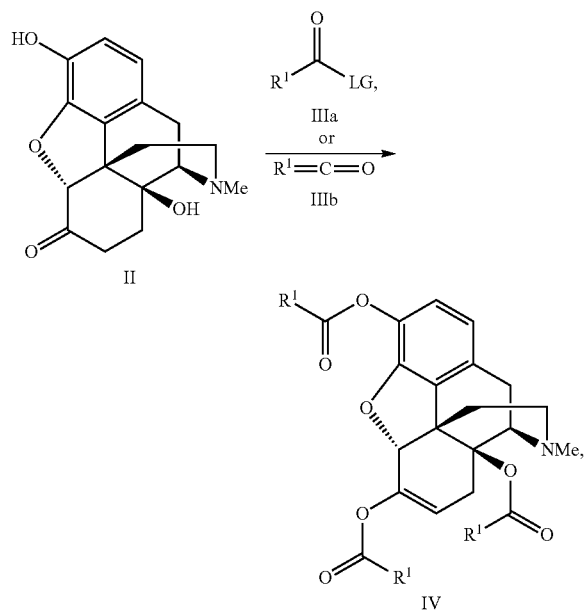

(b) reacting the compound of Formula IV with a metal catalyst in air and/or in the presence of an oxidant under conditions to provide a compound of Formula V:

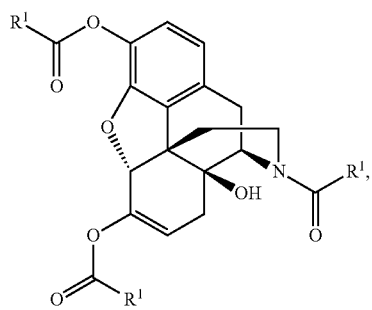

and
(c) treating the compound of Formula V with a reducing agent under conditions to provide the compound of Formula I, wherein each $R^1$ is selected from $C_{3-10}$cycloalkyl, $C_{1-10}$alkyl and $C_{6-10}$aryl, and each LG is a leaving group;
wherein in the compounds of the Formulae I, III, IV and V, one or more available hydrogens in $R^1$ is/are optionally replaced with F and/or one or more of available atoms in $R^1$ is/are optionally replaced with an isotopic label.

In an embodiment of the application, $R^1$ is selected from $C_{3-6}$cycloalkyl, $C_{1-6}$alkyl and phenyl. In another embodiment, $R^1$ is selected from cyclopropyl, cyclobutyl, cyclopentyl, methyl, ethyl, propyl, isopropyl, butyl, isobutyl, t-butyl and phenyl. In another embodiment, $R^1$ is selected from cyclopropyl and cyclobutyl, and the compound of Formula I is naltrexone or nalbuphone, respectively.

In an embodiment of the application, LG is any suitable leaving group. In a further embodiment, LG also electrophilically activates the adjacent carbonyl group for reaction with a nucleophile. In a further embodiment, LG is Cl, Br, CN, $CCl_3$, imidazole, pentafluorophenyl, acyl, $OC(O)R^1$, Ts, Ns, Ms, or any activating group for a carboxylic acid, for example activating groups used in peptide synthesis. In a specific embodiment, LG is halo or $OC(O)R^1$.

In an embodiment of the application, the conditions to provide a compound of Formula IV comprise combining the compound of Formula II with the compound of Formula IIIa or IIIb in the presence of a non-nucleophilic base in an inert solvent and at temperatures for the reaction of the compound of Formula II with the compound of Formula IIIa or IIIb to provide the compound of Formula IV. Examples of non-limiting reaction temperatures are about 0° C. to about 400° C., about 30° C. to about 200° C., or about 50° C. to about 110° C. Examples of non-limiting reaction times are about 0.5 hours to about 48 hours, or about 1 hour to about 24 hours. Examples of suitable bases include, but are not limited to, organic amines, such as triethylamine, pyridine, and 1,4-diazabicyclo[2.2.2]octane (DABCO) and inorganic bases, such as hydroxides, carbonates, and hydrogen carbonate under phase transfer conditions (i.e. the Schotten-Baumann reaction).

The conversion of the compound of the compound of Formula IV to the compound of Formula V involves a metal catalyzed demethylation of the 17 position nitrogen, followed by an intramolecular migration of the acyl group from the oxygen at C-14 to the 17 position nitrogen. Significantly, this transformation occurs in the absence of the addition of acylating reagents, such as $R^1C(O)$—O—$C(O)$—$R^1$. Accordingly, in an embodiment, the compound of Formula IV is reacted with reagents consisting essentially of, or consisting of, a metal catalyst and an oxygen source.

The metal catalyst is any suitable metal catalyst. In an embodiment, the catalyst is a transition metal catalyst. Examples of complexes/compounds which can be used as the catalyst include, but are not limited to, catalysts comprising palladium, platinum (e.g. $PtCl_2$ and $K_2PtCl_4$), ruthenium (e.g. Ru/C, $RuCl_3xH_2O$, $RuCl_2(PPh_3)_3$, $RuO_2$, and tetrapropylammonium perruthenates), iron (e.g. $FeCl_2$, $FeSO_4$, and iron carbonyls like $Fe_2(CO)_9$), tungsten (e.g. $Na_2WO_4$), vanadium (e.g. $VO(acac)_2$), iridium, copper, gold, and silver complexes. In an embodiment, the catalyst is a Pd(0) or Pd(II) catalyst, for example, but not limited to $Pd(OAc)_2$, $Pd(acac)_2$, Pd black or palladium-perovskites, or Pd(0) or Pd(II) catalysts on any type of solid support (e.g. charcoal, sulfates, carbonates, alumina) or in encapsulated form.

In another embodiment, the catalyst is used in an amount of about 0.1 mol % to about 20 mol %, about 1 mol % to about 15 mol % or about 5 mol % to about 10 mol %.

The conversion of the compound of Formula IV to the compound of Formula V is suitably carried out in the presence of an oxidant, either through the use of added $O_2$ gas or oxidant, or by simply carrying out the reaction in an air atmosphere. Examples of suitable oxidants, include, but are not limited to, organic and inorganic peroxides, such as t-butylhydroperoxide, cu men hydroperoxide, dibutylperoxide, laurylperoxide, hydrogenperoxide, perborates and $K_2S_2O_8$.

The conversion of the compound of Formula IV to the compound of Formula V is also suitably carried out in aqueous solutions or in an inert solvent or a mixture of solvents, such as, but not limited to, dioxane, toluene or benzene, DMF, $C_{1-6}$alkylOH, acetonitrile, diethylcarbonate, ionic liquids, water, dilute aqueous acid and dilute aqueous base, and at temperatures and time sufficient for the conversion to proceed to a sufficient extent. In a further embodiment, the solvent or mixture of solvents consists of, consists essentially of or comprises a $C_{1-4}$alcohol, in particular methanol, ethanol, n-propanol, 2-propanol, n-butanol, butan-2-ol or 2-methyl-1-propanol. Non-limiting examples of suitable temperatures are from about 10° C. to about 400° C., about 50° C. to about 200° C. or about 75° C. to about 125° C. Examples of non-limiting reaction times are about 0.5 hours to about 64 hours, about 1 hour to about 48 hours, or about 5 hours to about 30 hours. In a further embodiment of the application, the conversion of the compound of Formula IV to the compound of Formula V is carried out in the presence of a co-catalyst. Examples of co-catalysts include, but are not limited to copper salts such as copper acetate and copper chloride, and all oxophilic metals and their complexes, such as cerium salts.

The reduction of the compound of Formula V to the compounds of Formula I is carried out using any reducing agent suitable for reducing the 17 position carbonyl to a $CH_2$ group and for removing the acyl group on the 3 and 6 position hydroxyl groups, with concomitant rearrangement of the enol to the keto form. Examples of such reducing agents include, but are not limited to, metal hydride reducing agents including lithium aluminum hydride and sodium bis(2-methoxyethoxy)aluminum hydride, hydrosilylation reagents and hydroboration reagents. In an embodiment, the reduction is carried out using sodium bis(2-methoxyethoxy)aluminum hydride in an inert solvent or mixture of solvents at a temperature and for a time sufficient for the reduction to proceed to a sufficient extent. As a representative, non-limiting example, the temperature for the reduction of the compound of Formula V to the compound of Formula I is about 0° C. to about 400° C., about 20° C. to about 200° C., or about 50° C. to about 100° C. and examples of non-limiting reaction times are about 1 minute to about 24 hours, about 10 minutes to about 12 hours, or about 15 minutes to about 1 hour.

In an embodiment of the application, the compound of Formula II is oxymorphone which is readily available, for example, from oripavine or thebaine on an industrial scale[viii]. Compounds of Formula IIIa and IIIb are commercially available or may be prepared using methods known in the art. For example, carboxylic acid anhydrides may be prepared by reaction of the carboxylic acid, corresponding acyl chloride, and a base, such as triethylamine, in a nonpolar solvent system. The precipitated base hydrochloride can be filtered off and, after concentration of the filtrate, the product distilled under reduced pressure or purified using other known methods. This procedure is suitable for multigram preparation.

As a representative example of the process of the present application, an expedient route to naltrexone from oxymorphone was carried out that involved intramolecular acyl transfer during demethylation. Thus oxymorphone was peracylated either with cyclopropyl carboxylic acid anhydride, or with the corresponding acyl chloride, which is much less expensive, and converted to the fully acylated product. Exposure of this material to anhydride free conditions of N-demethylation provided an excellent yield of the N-acyl amide, isolated as a mixture of N-acyl diastereoisomers, whose reduction with Vitride™ (sodium bis(2-methoxyethoxy)aluminum hydride) furnished in 93% yield naltrexone. The N-demethylation/acylation protocol was subjected to a more detailed investigation. The reactions were conducted in the absence of additional cylopropylcarboxylic acid anhydride taking advantage of the intramolecular acyl transfer from the neighboring C-14 ester. A 92% yield of the N-acyl amide was obtained when Pd(C) was used in dioxane in the presence of air at 100° C. In DMF-water mixture (5:1) and Pd(OAC)$_2$ as a catalyst the yield of the N-acyl amide was 95% after 23 hours at 100° C. Somewhat lower yield (85%, with 7-8% recovery of the starting material) was obtained when Pd(C) was employed in DMF-water mixture. The full reduction of the N-acyl amide to naltrexone with Vitride™ deserves a comment. First of all, Vitride™ is a very convenient and inexpensive reducing agent, whose use at industrial scales is optimal compared to other, less safe reducing agents such as lithium aluminum hydride. Second, the reduction is extremely fast probably in part because of the anchimeric assistance of C-14 hydroxyl and reagent delivery through chelation.

The three-step transformation of oxymorphone to naltrexone proceeded with an overall yield of ~75% and can likely be further optimized, possibly even reduced to a one-pot procedure without isolation or purification.

The process of the present application may be extended to other C-14 hydroxy morphine analogs and the intramolecular transfer of other functional groups. Therefore, the present application also includes a process for the preparation of a compound of Formula VI:

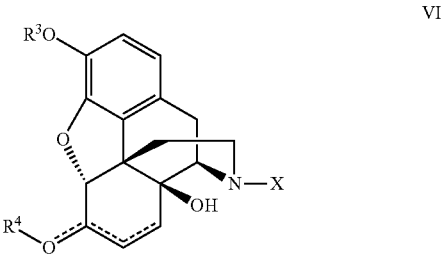

wherein

X is selected from $C(O)R^2$, $S(O)R^2$, $SO_2R^2$, $P(O)R^2R^{2'}$, $P(O)(OR^2)R^{2'}$ and $P(O)(OR^2)(OR^{2'})$;

$R^2$ and $R^{2'}$ are independently selected from $C_{3-10}$cycloalkyl, $C_{3-10}$heterocycloalkyl, $C_{3-10}$cycloalkenyl, $C_{1-10}$alkyl, $C_{2-10}$alkenyl, $C_{6-10}$aryl and $C_{5-10}$heteroaryl, each of the latter groups being unsubstituted or substituted with one or more substituents independently selected from $C_{1-4}$alkyl, $OC_{1-4}$ alkyl, halo, CN, $NO_2$, $C_{6-10}$aryl and $OC_{6-10}$aryl;

⸺ represents a single or double bond, provided that two double bonds are not adjacent to each other; and $R^3$ and $R^4$ are independently selected from $C_{1-10}$alkyl, $C_{6-10}$aryl, $C_{3-10}$cycloalkyl, $C_{1-10}$alkyleneC$_{6-10}$aryl, $C_{1-10}$alkyleneC$_{3-10}$cycloalkyl and PG, except when ⸺ represents =O, then $R^4$ is not present;

the process comprising:

(a) reacting a compound of Formula VII with a compound of Formula VIII(a) or VIII(b) under conditions to provide a compound of Formula IX:

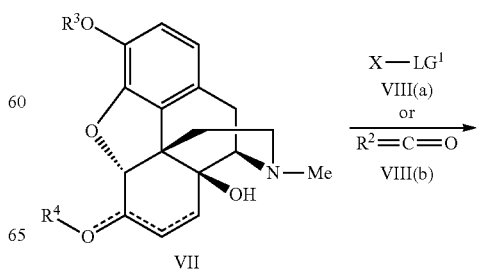

-continued

![Formula IX structure]

IX wherein $LG^1$ is a leaving group;
X is selected from $C(O)R^2$, $S(O)R^2$, $SO_2R^2$, $P(O)R^2R^{2'}$, $P(O)(OR^2)R^{2'}$ and $P(O)(OR^2)(OR^{2'})$;
$R^2$ and $R^{2'}$ are independently selected from $C_{3-10}$cycloalkyl, $C_{3-10}$heterocycloalkyl, $C_{3-10}$cycloalkenyl, $C_{1-10}$alkyl, $C_{2-10}$alkenyl, $C_{6-10}$aryl and $C_{5-10}$heteroaryl, each of the latter groups being unsubstituted or substituted with one or more substituents independently selected from $C_{1-4}$alkyl, $OC_{1-4}$alkyl, halo, CN, $NO_2$, $C_{6-10}$aryl and $OC_{6-10}$aryl;
═ represents a single or double bond, provided that two double bonds are not adjacent to each other; and $R^3$ and $R^4$ are independently selected from $C_{1-10}$alkyl, $C_{6-10}$aryl, $C_{3-10}$cycloalkyl, $C_{1-10}$alkyleneC$_{6-10}$aryl, $C_{1-10}$alkyleneC$_{3-10}$cycloalkyl and PG, except when ═ represents ═O, then $R^4$ is not present; and
(b) reacting the compound of Formula IX with a metal catalyst in the presence of an oxidant under conditions to provide the compound of Formula VI,
wherein in the compounds of Formulae VI, VII, VIII and IX, one or more available hydrogens in $R^2$, $R^{2'}$, $R^3$ and $R^4$ is/are optionally replaced with F and/or one or more of available atoms in $R^2$, $R^{2'}$, $R^3$ and $R^4$ is/are optionally replaced with an isotopic label.

In an embodiment of the application, $R^2$ and $R^{2'}$ are independently selected from $C_{3-6}$cycloalkyl, $C_{1-6}$alkyl and phenyl. In another embodiment, $R^2$ and $R^{2'}$ are independently selected from cyclopropyl, cyclobutyl, cyclopentyl, methyl, ethyl, propyl, isopropyl, butyl, isobutyl, t-butyl and phenyl. In another embodiment, $R^2$ and $R^{2'}$ are independently selected from cyclopropyl and cyclobutyl.

In an embodiment of the application, $LG^1$ is any suitable leaving group. In a further embodiment, $LG^1$ also electrophilically activates the adjacent group for reaction with a nucleophile. In a further embodiment, $LG^1$ is Cl, Br, CN, $CCl_3$, imidazole, pentafluorophenyl, acyl, O—X, Ts, Ns, Ms, or any activating group, for example activating groups used in peptide synthesis. In a specific embodiment, LG is Cl or O—X.

It is an embodiment that X is $C(O)R^2$.

In an embodiment, $R^3$ and $R^4$ are independently selected from $C_{1-6}$alkyl, phenyl, napthyl, $C_{3-6}$cycloalkyl, $C_{1-6}$alkyleneC$_{6-10}$aryl, $C_{1-6}$alkyleneC$_{3-6}$cycloalkyl and PG, except when ═ represents ═O, then $R^4$ is not present. In an embodiment, PG is a group that is compatible with the reaction conditions so that it is not removed or altered during the preparation of the compounds of Formula VI, but can be removed from the compounds of Formula VI upon completion of the process. Examples of suitable PG, include, but are not limited to, acyl, alkoxycarbonyl, Bn, methoxymethyl (MOM), alkyl carbonates and arylcarbonates.

In an embodiment, the compound of Formula VI is selected from a compound of Formula VI(a), VI(b) and VI(c):

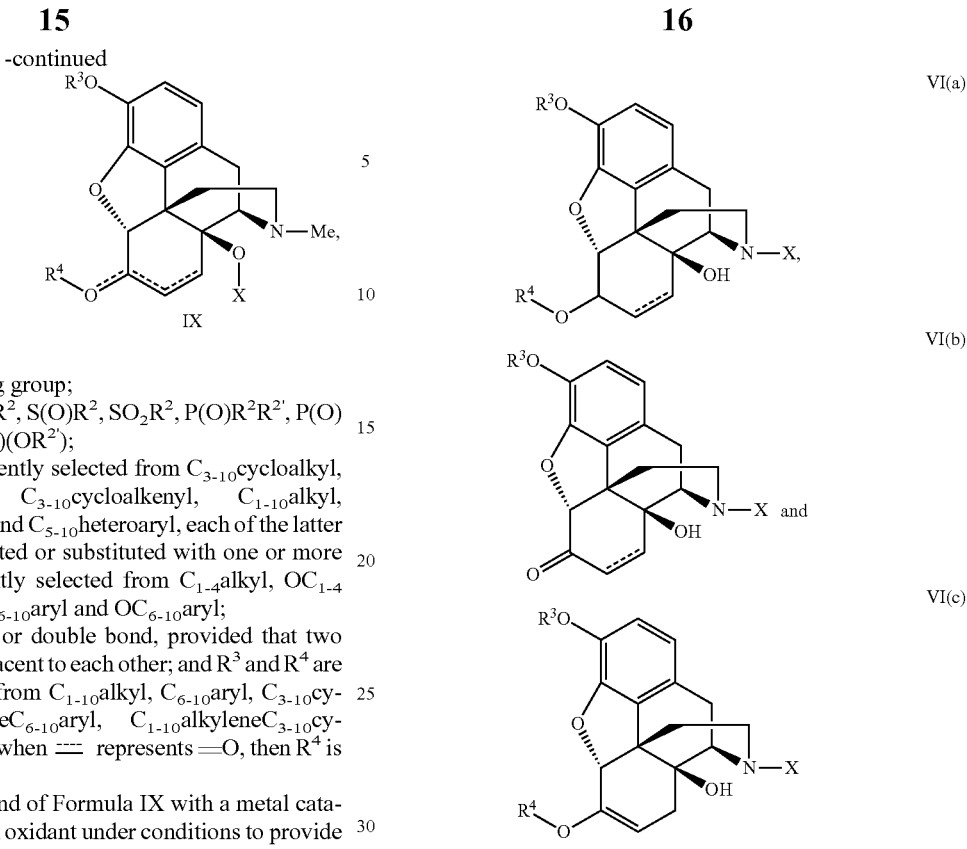

wherein
X is selected from $C(O)R^2$, $S(O)R^2$, $SO_2R^2$, $P(O)R^2R^{2'}$, $P(O)(OR^2)R^{2'}$ and $P(O)(OR^2)(OR^{2'})$;
$R^2$ and $R^{2'}$ are independently selected from $C_{3-10}$cycloalkyl, $C_{3-10}$heterocycloalkyl, $C_{3-10}$cycloalkenyl, $C_{1-10}$alkyl, $C_{2-10}$alkenyl, $C_{6-10}$aryl and $C_{5-10}$heteroaryl, each of the latter groups being unsubstituted or substituted with one or more substituents independently selected from $C_{1-4}$alkyl, $OC_{1-4}$alkyl, halo, CN, $NO_2$, $C_{6-10}$aryl and $OC_{6-10}$aryl;
═ represents a single or double bond;
$R^3$ and $R^4$ are independently selected from $C_{1-10}$alkyl, $C_{6-10}$aryl, $C_{3-10}$cycloalkyl, $C_{1-10}$alkyleneC$_{6-10}$aryl, $C_{1-10}$alkyleneC$_{3-10}$cycloalkyl and PG, and
one or more available hydrogens in $R^2$, $R^{2'}$, $R^3$ and $R^4$ is/are optionally replaced with F and/or one or more of available atoms in $R^2$, $R^{2'}$, $R^3$ and $R^4$ is/are optionally replaced with an isotopic label.

In another embodiment, the compound of Formula VI is a compound of Formula VI(a) or VI(b) wherein ═ represents a single bond.

In an embodiment of the application, the conditions to provide a compound of Formula IX comprise combining the compound of Formula VII with the compound of Formula VIII(a) or VIII(b) in the presence of a non-nucleophilic base in an inert solvent and at temperatures for the reaction of the compound of Formula VII with the compound of Formula VIII(a) or VIII(b) to provide the compound of Formula IX. Examples of non-limiting reaction temperatures are about 0° C. to about 400° C., about 30° C. to about 200° C., or about 50° C. to about 110° C. Examples of non-limiting reaction times are about 0.5 hours to about 48 hours, or about 1 hour to about 24 hours. Examples of suitable bases include, but are not limited to, organic amines, such as triethylamine, pyridine, and 1,4-diazabicyclo[2.2.2]octane (DABCO) and inorganic bases, such as hydroxides, carbonates, and hydrogen carbonate under phase transfer conditions (i.e. the Schotten-Baumann reaction).

The conversion of the compound of the compound of Formula IX to the compound of Formula VI involves a metal-catalyzed demethylation of the 17 position nitrogen, followed by an intramolecular migration of the "—X" group from the oxygen at C-14 to the 17 position nitrogen. Significantly, this transformation occurs in the absence of the addition of reagents, such as $R^2C(O)$—O—$C(O)$—$R^2$, $R^2$—$S(O)$—O—$S(O)$—$R^2$, $R^2$—$SO_2$—O—$SO_2$—$R^2$, Cl—$P(O)R^2R^{2'}$, Cl—$P(O)(OR^2)R^{2'}$ and Cl—$P(O)(OR^2)(OR^2)$. Accordingly, in an embodiment, the compound of Formula IX is reacted with reagents consisting essentially of, or consisting of, a metal catalyst and an oxidant.

The metal catalyst is any suitable metal catalyst. In an embodiment, the catalyst is a transition metal catalyst. Examples of complexes/compounds which can be used as the catalyst include, but are not limited to, catalysts comprising palladium, platinum (e.g. $PtCl_2$ and $K_2PtCl_4$), ruthenium (e.g. Ru/C, $RuCl_3xH_2O$, $RuCl_2(PPh_3)_3$, $RuO_2$, and tetrapropylammonium perruthenates), iron (e.g. $FeCl_2$, $FeSO_4$, and iron carbonyls like $Fe_2(CO)_9$), tungsten (e.g. $Na_2WO_4$), vanadium (e.g. $VO(acac)_2$), iridium, copper, gold, and silver complexes. In an embodiment, the catalyst is a Pd(0) or Pd(II) catalyst, for example, but not limited to $Pd(OAc)_2$, $Pd(acac)_2$, Pd black or palladium-perovskites, or Pd(0) or Pd(II) catalysts on any type of solid support (e.g. charcoal, sulfates, carbonates, alumina) or in encapsulated form.

In another embodiment, the catalyst is used in an amount of about 0.1 mol % to about 20 mol %, about 1 mol % to about 15 mol % or about 5 mol % to about 10 mol %.

The conversion of the compound of Formula IX to the compound of Formula VI is suitably carried out in the presence of an oxidant, either through the use of added $O_2$ gas or oxidant, or by simply carrying out the reaction in an air atmosphere. Examples of suitable oxidants, include, but are not limited to organic and inorganic peroxides, such as t-butylhydroperoxide, cumenhydroperoxide, dibutylperoxide, laurylperoxide, hydrogenperoxide, perborates and $K_2S_2O_8$.

The conversion of the compound of Formula IX to the compound of Formula VI is also suitably carried out in aqueous solutions or in an inert solvent or a mixture of solvents, such as, but not limited to, dioxane, toluene or benzene, DMF, $C_{1-6}$alkylOH, acetonitrile, diethylcarbonate, ionic liquids, water, dilute aqueous acid and dilute aqueous base, and at temperatures and time sufficient for the conversion to proceed to a sufficient extent. In a further embodiment, the solvent or mixture of solvents consists of, consists essentially of or comprises a $C_{1-4}$alcohol, in particular methanol, ethanol, n-propanol, 2-propanol, n-butanol, butan-2-ol or 2-methyl-1-propanol. Non-limiting examples of suitable temperatures are from about 10° C. to about 400° C., about 50° C. to about 200° C. or about 75° C. to about 125° C. Examples of non-limiting reaction times are about 0.5 hours to about 64 hours, about 1 hour to about 48 hours, or about 5 hours to about 30 hours. In a further embodiment of the application, the conversion of the compound of Formula IX to the compound of Formula VI is carried out in the presence of a co-catalyst. Examples of co-catalysts include, but are not limited to copper salts such as copper acetate and copper chloride, and all oxophilic metals and their complexes, such as cerium salts.

The compounds of Formula VI are useful intermediates in the preparation of morphine alkaloids. For example, in one embodiment, the "—X" group may selectively be removed, via acid or base hydrolysis, from N-17, to provide the corresponding secondary amine of Formula X:

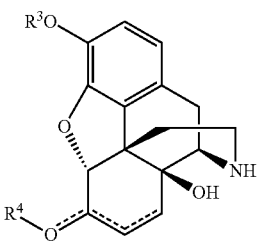

X wherein $\equiv$ represents a single or double bond, provided that two double bonds are not adjacent to each other;

$R^3$ and $R^4$ are independently selected from $C_{1-10}$alkyl, $C_{6-10}$aryl, $C_{3-10}$cycloalkyl, $C_{1-10}$alkylene$C_{6-10}$aryl, $C_{1-10}$alkylene$C_{3-10}$cycloalkyl and PG, except when $\equiv$ represents =O, then $R^4$ is not present; and one or more available hydrogens in $R^3$ and $R^4$ is/are optionally replaced with F and/or one or more of available atoms in $R^3$ and $R^4$ is/are optionally replaced with an isotopic label. The N-17 secondary amine may then be selectively alkylated with any number of alkylating reagents to provide a variety of substituents at this position. The process is particularly useful for exploring the structure activity relationship of different groups at this location. In an embodiment, the N-17 secondary amine of the compound of Formula X is selectively alkylated with a cyclopropylmethyl, cyclobutylmethyl or allyl group.

In another embodiment, compounds of Formula VI(a), VI(b) or VI(c) wherein X is "—$C(O)R^2$" may be reduced, to provide the corresponding compound of Formula XI(a), XI(b) or XI(c), respectively:

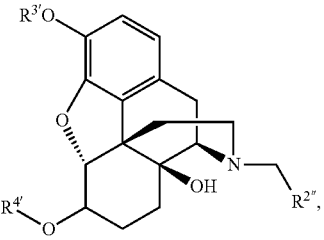

XI(a)

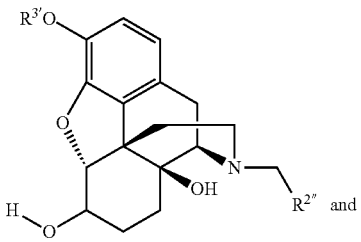

XI(b) and

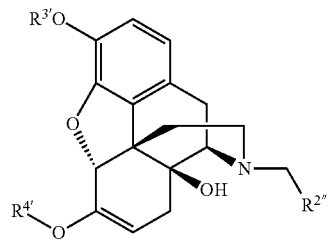

XI(c)

wherein

R$^{2''}$ is selected from C$_{3-10}$cycloalkyl, C$_{3-10}$heterocycloalkyl, C$_{1-10}$alkyl, C$_{6-10}$aryl and C$_{5-10}$heteroaryl, each of the latter groups being unsubstituted or substituted with one or more substituents independently selected from C$_{1-4}$alkyl, OC$_{1-4}$alkyl, halo, CN, NO$_2$, C$_{6-10}$aryl and OC$_{6-10}$aryl;

R$^{3'}$ and R$^{4'}$ are independently selected from C$_{1-10}$alkyl, C$_{6-10}$aryl, C$_{3-10}$cycloalkyl, C$_{1-10}$alkyleneC$_{6-10}$aryl, C$_{1-10}$alkyleneC$_{3-10}$cycloalkyl and PG; and one or more available hydrogens in R$^{2''}$, R$^{3'}$ and R$^{4'}$ is/are optionally replaced with F and/or one or more of available atoms in R$^{2''}$, R$^{3'}$ and R$^{4'}$ is/are optionally replaced with an isotopic label, wherein when PG is a protecting group that is removed by the reducing agent, R$^{3'}$ and R$^{4'}$ are H and the compound of Formula XI(c) converts to the ketone form.

In another embodiment of the present application, when one or both of R$^{3'}$ and R$^{4'}$ are PG, the processes of the present application further include removal of the protecting groups to provide the free "—OH" compounds.

The processes of the present application may be performed using continuous or batch processes. For commercial scale preparations continuous processes are suitable. Methods of performing chemical processes in continuous or batch modes are known in the art. When continuous processes are used, the reaction temperature and/or pressure may be higher than those used in batch processes.

III. Compounds of the Application

The present application also includes compounds of Formula IV and V, useful for the preparation of compounds of Formula I.

Accordingly, the present application includes a compound of Formula IV or V:

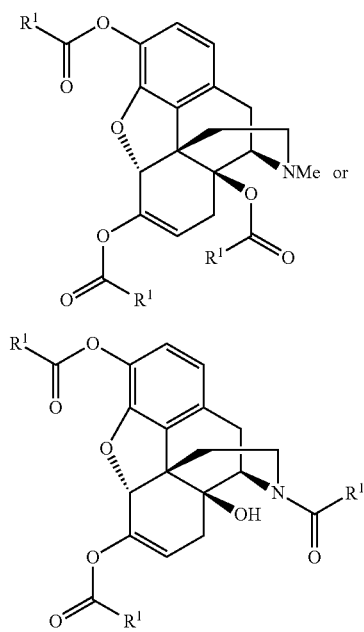

wherein R$^1$ is, independently, selected from C$_{3-10}$cycloalkyl, C$_{1-10}$alkyl and C$_{6-10}$aryl.

In an embodiment of the application, R$^1$ in the compound of Formula IV or V is, independently selected from C$_{3-6}$cycloalkyl, C$_{1-6}$alkyl and phenyl. In another embodiment, R$^1$ in the compound of Formula IV or V is, independently selected from cyclopropyl, cyclobutyl, cyclopentyl, methyl, ethyl, propyl, isopropyl, butyl, isobutyl, t-butyl and phenyl. In another embodiment, R$^1$ in the compound of Formula IV or V is, independently selected from cyclopropyl and cyclobutyl.

The following non-limiting examples are illustrative of the present application:

EXAMPLES

Example 1

3,14-Diacetyloxymorphone

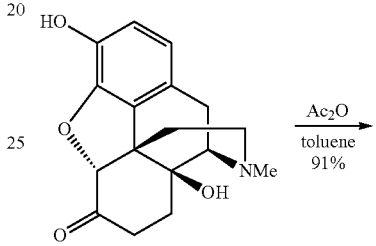

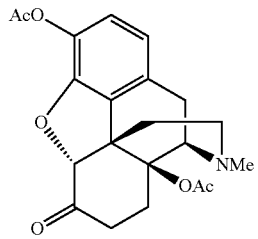

A suspension of oxymorphone (3.20 g; 10.63 mmol), acetic anhydride (8.68 g; 85.04 mmol) and toluene (30 mL) was placed into a pre-heated oil bath at 80° C. After 15 mins of stirring all solid dissolved and the pale yellow solution was stirred at 80° C. for 1 h, after which time it was allowed to stir overnight at room temperature. The excess anhydride was removed by azeotropic distillation with toluene and the mixture was concentrated to a thick slurry, which was dissolved in dichloromethane. This solution was washed with sat. NaHCO$_3$ (10 mL) and the aqueous layer was extracted with dichloromethane. (3×5 mL). Combined organic layers were washed with water, brine, dried over Na$_2$SO$_4$ and concentrated. Crystallization from EtOH (12 mL) and MeOH (3 mL) afforded 3.48 g of product. The mother liquor was concentrated and chromatographed (eluent EtOAc+10% MeOH). Crystallization of collected material afforded additional 0.27 g of product for the overall yield of 91% of the title compound.

mp 218-220° C. (EtOH); R$_f$ 0.53 (ethyl acetate+20% methanol); [α]$^{22}_D$=−180.00 (c=1.0, CHCl$_3$); IR (CHCl$_3$) v 3027, 2936, 2805, 1761, 1728, 1626, 1446, 1370, 1216, 1156 cm$^{-1}$; $^1$H NMR (600 MHz, CDCl$_3$) 6.87 (d, J=8.1 Hz, 1H), 6.71 (d, J=8.1 Hz, 1H), 4.69 (s, 1H), 4.22 (d, J=5.4 Hz, 1H), 3.25 (d, J=18.8 Hz, 1H), 2.82 (ddd, J=14.3, 5.0, 2.6 Hz, 1H), 2.63 (ddd, J=14.7, 14.7, 5.4 Hz, 1H), 2.56-2.46 (m, 3H), 2.33 (s, 3H), 2.32 (s, 3H), 2.31 (m, 1H), 2.19 (s, 3H), 2.17 (m, 1H), 1.64 (ddd, J=14.2, 14.2, 3.8 Hz, 1H), 1.55 (m, 1H); $^{13}$C NMR (150 MHz, CDCl$_3$) δ 206.51, 170.22, 168.45, 147.65, 132.53, 131.30, 129.02, 123.14, 119.55, 90.23, 82.15, 57.62, 50.32, 45.42, 42.68, 35.52, 30.07, 26.78, 22.60, 22.24, 20.83; MS (+FAB) m/z (%): 43 (52), 326 (100), 343 (72), 386 (65); HRMS calcd for C$_{21}$H$_{23}$NO$_6$$^+$ 386.1598. found 386.15627.

Example 2

3,17-diacetyl-noroxymorphone

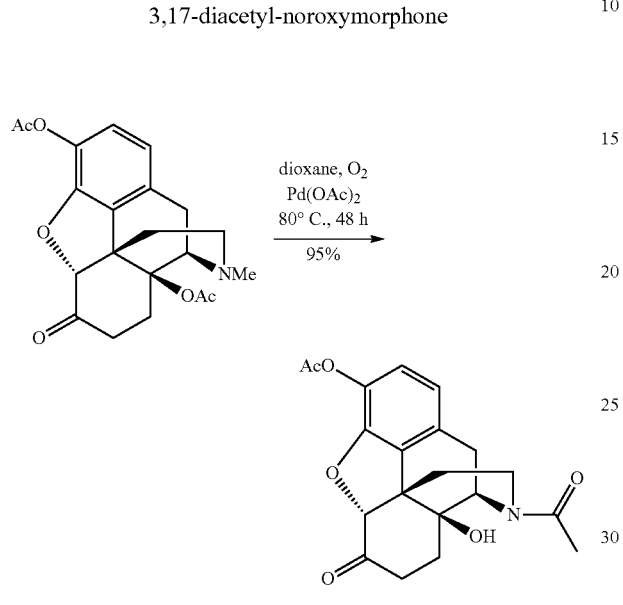

A mixture of 3,14-diacetyloxymorphone (Example 1, 1.0 g; 2.594 mmol), Pd(OAc)$_2$ (0.011 g; 0.052 mmol) and dioxane (10 mL) was stirred at 80° C. under oxygen atmosphere for two days. When the TLC analysis showed that the starting material disappeared, the mixture was concentrated to a thick oil and loaded onto a chromatography column. Chromatography (eluent EtOAc+10% MeOH) afforded 0.89 g (92%) of white solid as a 1:4 mixture of the title compound; mp>235° C. (EtOH); R$_f$ 0.32 (ethyl acetate+10% methanol; IR (CHCl$_3$) v 3364, 3025, 3009, 2957, 2933, 1762, 1728, 1622, 1443, 1370, 1156, 1036 cm$^{-1}$;

Major Isomer:

$^1$H NMR (600 MHz, CDCl$_3$) δ 6.90 (d, J=8.2 Hz, 1H), 6.75 (d, J=8.2 Hz, 1H), 5.10 (d, J=5.9 Hz, 1H), 4.73 (s, 1H), 4.35 (s, 1H), 3.66 (dd, J=14.0, 4.8 Hz, 1H), 3.15-3.04 (m, 3H), 2.88 (d, J=18.7 Hz, 1H), 2.63 (ddd, J=12.6, 12.6, 5.2 Hz, 1H), 2.33 (s, 3H), 2.30 (m, 1H), 2.16 (s, 3H), 2.02 (m, 1H), 1.70 (ddd, J=14.0, 14.0, 3.4 Hz, 1H), 1.58 (dd, J=12.6, 3.0 Hz, 1H); $^{13}$C NMR (150 MHz, CDCl$_3$) δ 207.27, 171.15, 168.53, 147.94, 132.92, 129.52, 129.37, 123.52, 119.89, 90.19, 70.48, 53.32, 50.35, 39.98, 35.71, 31.79, 31.73, 28.84, 22.18, 20.83;

Minor Isomer:

$^1$H NMR (600 MHz, CDCl$_3$) δ 6.90 (d, J=8.2 Hz, 1H), 6.75 (d, J=8.2 Hz, 1H), 4.73 (s, 1H), 4.48 (dd, J=14.3, 4.9 Hz, 1H), 4.35 (s, 1H), 4.11 (d, J=5.6 Hz, 1H), 3.71 (m, 1H), 3.20 (dd, J=18.6, 5.9 Hz, 1H), 3.11 (m, 1H), 3.01 (d, J=18.4 Hz, 1H), 2.55 (ddd, J=13.6, 13.6, 4.2 Hz, 1H), 2.38 (m, 1H), 2.25 (s, 3H), 1.97 (m, 1H), 1.71-1.66 (m, 2H); $^{13}$C NMR (150 MHz, CDCl$_3$) δ 206.93, 170.89, 168.40, 147.94, 133.06, 129.27, 128.67, 123.71, 119.82, 90.12, 70.83, 59.68, 50.35, 39.98, 34.42, 32.42, 31.13, 28.84, 22.32, 20.82;

MS (+EI) m/z (%): 43 (63), 84 (100), 244 (13), 287 (4), 311 (4), 329 (34), 371 (7); HRMS calcd for C$_{20}$H$_{21}$NO$_6$ 371.1369. found 371.13633.

Example 3

3,6,14-Tris(cyclopropylcarboxy)oxymorphone

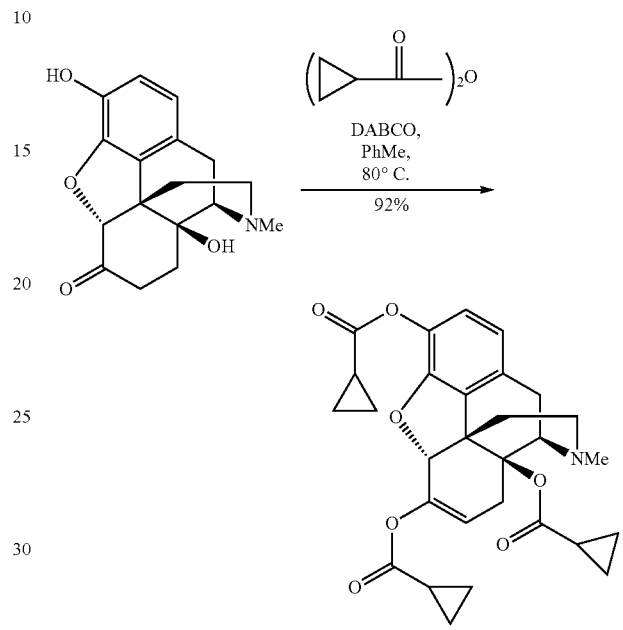

A suspension of oxymorphone (1.56 g; 5.19 mmol), cyclopropylcarboxylic acid anhydride (4.0 g; 25.95 mmol), and toluene (20 mL) was stirred at 80° C. for 160 min. Then DABCO was added in one portion (1.16 g; 10.38 mmol) and the resulting mixture was stirred at 80° C. over 15 h. After this time the conversion was incomplete and an additional amount of anhydride (1.60 g; 10.38 mmol) was added and mixture was stirred at 80° C. for 5 h. Then the reaction mixture was allowed to cool down, concentrated in vacuo, and the excess anhydride was removed under high vacuum. The mixture was diluted with dichloromethane (20 mL), washed with sat. NaHCO$_3$ (5 mL) and the aqueous layer was extracted with dichloromethane (3×5 mL). Combined organic layers were washed with water, brine, dried over Na$_2$SO$_4$ and concentrated. Column chromatography (eluent EtOAc→EtOAc+ 10% MeOH) afforded 2.37 g (90%) of the title compound as a white solid.

This reaction could also be performed using cyclopropylcarboxylic acid chloride (less expensive) and triethylamine in ethyl acetate as the solvent at 80° C. to obtain 92% of the titled compound.

mp 158-160° C. (EtOH); R$_f$ 0.40 (ethyl acetate:hexane/1: 1); [α]$^{22}_D$=−122.96 (c=1.0, CHCl$_3$); IR (CHCl$_3$) v 3025, 2934, 2849, 1743, 1716, 1440, 1387, 1100, 1032 cm$^{-1}$; $^1$H NMR (600 MHz, CDCl$_3$) δ 6.86 (d, J=8.2 Hz, 1H), 6.67 (d, J=8.2 Hz, 1H), 5.42 (dd, J=6.0, 1.6 Hz, 1H), 5.08 (s, 1H), 4.22 (d, J=6.0 Hz, 1H), 3.21 (d, J=18.8 Hz, 1H), 3.05 (dd, J=18.3, 6.2 Hz, 1H), 2.55 (dd, J=18.8, 6.2 Hz, 1H), 2.47 (dd, J=11.8, 4.7 Hz, 1H), 2.38 (ddd, J=12.3, 12.3, 5.2 Hz, 1H), 2.31 (s, 3H), 2.22 (ddd, J=12.0, 12.0, 3.4 Hz, 1H), 2.04 (d, J=18.4 Hz, 1H), 1.87 (m, 1H), 1.77-1.69 (m, 1H), 1.65-1.58 (m, 2H), 1.21 (m, 1H), 1.18 (m, 1H), 1.14-1.09 (m, 3H), 1.05 (m, 1H), 1.04-1.00 (m, 2H), 0.99-0.94 (m, 2H), 0.90-0.82 (m, 2H); $^{13}$C NMR (150 MHz, CDCl$_3$) δ 174.08, 173.21, 172.47, 147.37, 143.85, 133.30, 131.59, 130.69, 122.69, 118.87, 116.56, 86.88, 81.02, 57.45, 47.06, 45.07, 42.87, 30.28, 27.27, 22.96, 14.52, 12.97, 12.81, 9.367, 9.23, 9.16, 9.05, 8.55, 8.43; MS (+EI) m/z (%): 41 (48), 56 (55), 69 (100), 86 (100), 124 (20), 167 (16), 437 (16), 505 (12); HRMS calcd for C$_{29}$H$_{31}$NO$_7$ 505.2101. found 505.21049.

Example 4

3,6,17-Tris(cyclopropylcarboxy)oxymorphone

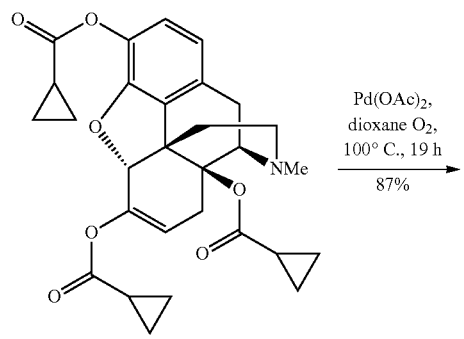

A mixture of 3,6,14-tris(cyclopropylcarboxy)oxymorphone (1.0 g; 1.98 mmol), Pd(OAc)$_2$ (0.009 g; 0.004 mmol), and dioxane (10 mL) was stirred at 100° C. over 24 h under oxygen atmosphere. After 5 min of stirring a thick Pd black precipitate was observed. When the starting material disappeared (vide TLC) the mixture was concentrated and loaded onto a column. Column chromatography (eluent EtOAc) afforded 0.85 g (87%) of the title compound as a mixture (1:4) of amide isomers that was easy to crystallize; mp 130-133° C. (MeOH); R$_f$ 0.46 (ethyl acetate); IR (CHCl$_3$) v 3573, 3419, 3013, 2919, 1747, 1618, 1448, 1386, 1149, 1032.

The N-demethylation/acylation protocol was subjected to more detailed investigation. The reactions were conducted in the absence of additional cylopropylcarboxylic acid anhydride taking advantage of the intramolecular acyl transfer from the neighboring C-14 ester. A 92% yield of the title compound was obtained when Pd(C) was used in dioxane in the presence of air at 100° C. In DMF-water mixture (5:1) and Pd(OAC)$_2$ as a catalyst the yield of the title compound was 95% after 23 hours at 100° C. Somewhat lower yield (85%, with 7-8% recovery of the starting material) was obtained when Pd(C) was employed in DMF-water mixture.

Major Isomer:
1H NMR (600 MHz, CDCl$_3$) δ 6.89 (d, J=8.0 Hz, 1H), 6.68 (d, J=8.0 Hz, 1H), 5.53 (s, 1H), 5.10 (m, 1H), 5.07 (s, 1H), 4.07 (d, J=11.0 Hz, 1H), 3.30-3.13 (m, 2H), 2.89 (d, J=18.6 Hz, 1H), 2.51 (m, 1H), 2.24 (m, 1H), 2.17 (m, 1H), 1.86 (m, 1H), 1.78 (m, 1H), 1.72 (m, 1H), 1.65 (m, 1H), 1.24-1.14 (m, 2H), 1.09 (m, 2H), 1.05 (m, 2H), 1.00-0.91 (m, 4H), 0.78 (m, 2H); $^{13}$C NMR (150 MHz, CDCl$_3$) δ 174.07, 173.17, 172.48, 147.69, 143.44, 133.59, 131.05, 130.05, 123.08, 119.19, 117.26, 86.72, 71.24, 53.62, 47.44, 38.73, 32.71, 32.44, 29.37, 12.95, 12.81, 11.75, 9.39, 9.27, 9.17, 9.05, 7.76, 7.41.

Minor Isomer:
$^1$H NMR (600 MHz, CDCl$_3$) δ 6.89 (d, J=8.0 Hz, 1H), 6.68 (d, J=8.0 Hz, 1H), 5.53 (s, 1H), 5.01 (s, 1H), 4.47 (m, 1H), 3.27 (m, 1H), 3.03 (d, J=18.3 Hz, 1H), 2.65 (dd, J=12.0, 11.0 Hz, 1H), 2.38-2.12 (m, 3H), 1.90-1.63 (m, 4H), 1.24-1.14 (m, 2H), 1.09 (m, 2H), 1.05 (m, 2H), 1.00-0.91 (m, 4H), 0.78 (m, 2H); $^{13}$C NMR (150 MHz, CDCl$_3$) δ 174.07, 173.35, 172.39, 147.69, 143.69, 133.69, 131.05, 129.52, 123.21, 119.19, 117.15, 86.60, 71.11, 57.52, 47.58, 34.79, 33.11, 32.14, 28.64, 12.95, 12.81, 11.75, 9.39, 9.27, 9.17, 9.05, 7.77, 7.22; MS (+EI) m/z (%): 41 (36), 69 (100), 112 (9), 226 (6), 294 (3), 354 (4), 423 (5), 491 (10); HRMS calcd for C$_{28}$H$_{29}$NO$_7$ 491.1944. found 491.19479.

Example 5

Naltrexone

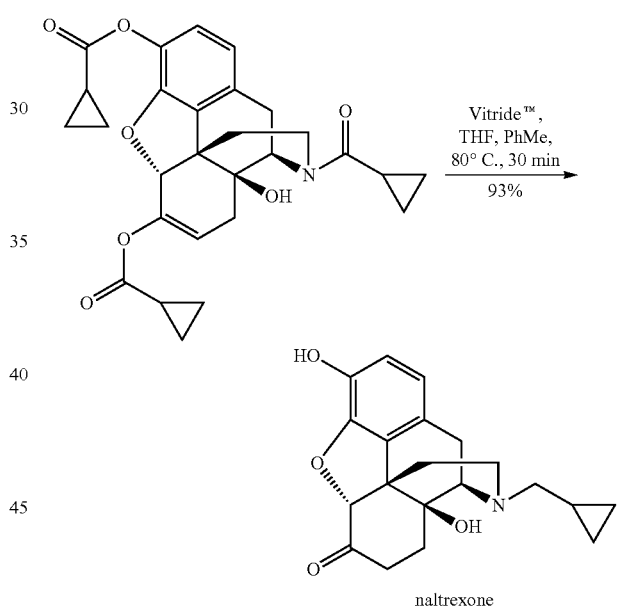

naltrexone

A flame-dried flask thoroughly purged with nitrogen was charged with Vitride™ (0.76 g of 65% solution in toluene; 2.44 mmol). A solution of amide 3,6,17-tris(cyclopropylcarboxy)oxymorphone (0.20 g; 0.407 mmol) in THF (2 mL) was added over 30 sec. When bubbling ceased the mixture was placed into a pre-heated oil bath at 80° C. After refluxing for 30 min the mixture was allowed to cool down, quenched with cold solution of Rochell's salt (2 mL), water (2 mL), and diluted with dichloromethane (3 mL). After extraction and separation of organic layer sat. NH$_4$Cl (0.5 mL) was added to the aqueous layers and product was extracted with dichloromethane. Addition of solution of NH$_4$Cl (0.5 mL) and extraction was repeated three times. The combined organic layers were washed with water, brine, dried over Na$_2$SO$_4$ and concentrated. Naltrexone, 0.13 g (93%), was obtained by column chromatography (eluent EtOAc+20% MeOH) as a white solid.

Vitride™ is a very convenient and inexpensive reducing agent, whose use at industrial scales is optimal to other, less safe reducing agents such as lithium aluminum hydride. The reduction is extremely fast probably in part because of the anchimeric assistance of C-14 hydroxyl and reagent delivery through chelation.

mp 159-161° C. (MeOH), [lit. mp 174-176° C. (acetone)][ix]; $R_f$ 0.42 (ethyl acetate+20% MeOH); $[\alpha]^{20}_D$=-207.00 (c=1, CHCl$_3$); IR (CHCl$_3$) v 3568, 3359, 3010, 2931, 2834, 1723, 1620, 156, 1317, 1146, 1058, 943; $^1$H NMR (600 MHz, CDCl$_3$) δ 6.74 (d, J=8.1 Hz, 1H), 6.60 (d, J=8.1 Hz, 1H), 5.82 (bs, 1H, OH), 4.74 (s, 1H), 3.21 (d, J=5.9 Hz, 1H), 3.11-3.03 (m, 2H), 2.72 (dd, J=12.0, 4.8 Hz, 1H), 2.58 (dd, J=18.4, 6.0 Hz, 1H), 2.49-2.39 (m, 3H), 2.34 (ddd, J=14.5, 3.0, 3.0 Hz, 1H), 2.18 (ddd, J=12.2, 3.8, 3.8 Hz, 1H), 1.91 (m, 1H), 1.66 (ddd, J=14.2, 14.2, 3.3 Hz, 1H), 1.59 (ddd, J=12.8, 2.7 Hz, 1H), 0.88 (m, 1H), 0.57 (m, 2H), 0.16 (m, 2H); $^{13}$C NMR (150 MHz, CDCl$_3$) δ 210.02, 142.51, 138.80, 129.05, 124.25, 119.90, 117.91, 90.60, 70.32, 62.01, 59.21, 51.07, 43.60, 36.21, 31.36, 30.65, 22.62, 9.42, 4.02, 3.81; MS (+EI) m/z (%): 47 (15), 55 (41, 84 (100), 110 (12), 202 (5), 256 (12), 286 (7), 300 (15), 341 (64); HRMS calcd for C$_{20}$H$_{23}$NO$_4$ 341.1627. found 341.16320.

While the present application has been described with reference to what are presently considered to be the preferred examples, it is to be understood that the application is not limited to the disclosed examples. To the contrary, the application is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety. Where a term in the present application is found to be defined differently in a document incorporated herein by reference, the definition provided herein is to serve as the definition for the term.

FULL CITATIONS FOR DOCUMENTS REFERRED TO IN THE APPLICATION

[i] Von Braun, J. Chem. Ber. 1980, 33, 1438.
[ii] Cooley, J. H.; Evain, E. J. Synthesis 1989, 1; Olofson, R. A. et al. J. Org. Chem. 1984, 49, 2081.
[iii] Ripper, J. A., et al. Biorg. & Med. Chem. Lett. 2001, 11, 443-445.
[iv] (a) Kok, G. et al. Adv. Synth. Catal. 2009, 351, 283; (b) Dong, Z. et al. J. Org. Chem. 2007, 72, 9881; (c) Smith, C. et al. PCT Patent Application Publication No. WO 2005/028483.
[v] (a) Madyashtha, K. M. et al. Proc. Indian Acad. Sci. 1984, 106, 1203; (b) Madyastha, K. M. et al. J. Chem. Soc. Perkin Trans. 1, 1994, 911.
[vi] Chaudhary, V. et al. Collect. Czech. Chem. Commun. 2009, 74, 1179.
[vii] (a) Carroll, R. J. et al. Adv. Synth. Catal. 2008, 350, 2984; (b) Carroll, R. J. et al. U. S. Patent Application Publication No. US 2009/0005565.
[viii] References for the formation of oxymorphone from oripavine: Dung et al. U.S. Pat. No. 7,851,482; Huang, US 20080125592, US 20100274019, US 20110009634; Wang et al. US 20100113787. References for the formation of oxymorphone from thebaine via 14-hydroxycodeinone: Weiss et al. J. Org. Chem. 1957, 22, 1505-8.
[ix] (a) Pillai, O.; Hamad, M. O.; Crooks, P. A.; Stinchcomb, A. L. Pharm. Res., 2004, 21, 1146; (b) Hamad, M. O.; Kiptoo, P. K.; Stinchcomb, A. L.; Crooks, P. A.; Bioorg. Med. Chem. 2006, 14, 7051

We claim:

1. A process for the preparation of a compound of Formula I:

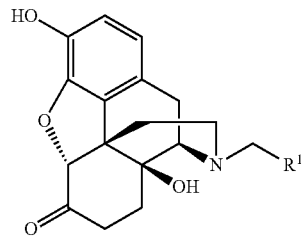

comprising:
(a) reacting a compound of Formula II with a compound of Formula IIIa or IIIb under conditions to provide a compound of Formula IV:

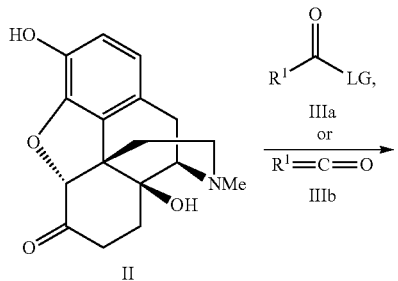

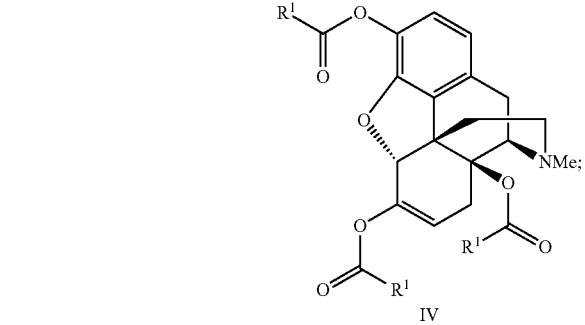

(b) reacting the compound of Formula IV with a metal catalyst in the presence of an oxidant under conditions to provide a compound of Formula V:

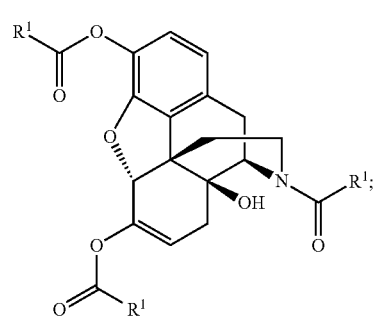

and
(c) treating the compound of Formula V with a reducing agent under conditions to provide the compound of Formula I, wherein each $R^1$ is selected from $C_{3-10}$cycloalkyl, $C_{1-10}$alkyl and $C_{6-10}$aryl, and each LG is a leaving group;

wherein in the compounds of the Formulae I, III, IV and V, one or more available hydrogens in $R^1$ is/are optionally replaced with F and/or one or more of available atoms in $R^1$ is/are optionally replaced with an isotopic label.

2. The process of claim 1, wherein $R^1$ is selected from $C_{3-6}$cycloalkyl, $C_{1-6}$alkyl, and phenyl.

3. The process of claim 2, wherein $R^1$ is selected from cyclopropyl, cyclobutyl, cyclopentyl, methyl, ethyl, propyl, isopropyl, butyl, isobutyl, t-butyl and phenyl.

4. The process of claim 3, wherein $R^1$ is selected from cyclopropyl and cyclobutyl, and the compound of Formula I is naltrexone or nalbuphone, respectively.

5. The process of claim 1, wherein LG is halo or O—C(O)$R^1$.

6. The process of claim 1, wherein the metal catalyst is a catalyst comprising palladium, platinum, ruthenium, iron, tungsten, vanadium, copper, gold, and silver complexes.

7. The process of claim 6, wherein the palladium catalyst is a Pd(0) or Pd(II) catalyst.

8. The process of claim 7, wherein the Pd(0) or Pd(II) catalyst, is Pd(OAc)$_2$, Pd(acac)$_2$, Pd black or Pd-pervoskites, and the Pd catalyst is optionally supported on a solid support or is in encapsulated form.

9. The process of claim 1 wherein the conditions to provide a compound of Formula IV comprise combining the compound of Formula II with the compound of Formula IIIa or IIIb in the presence of a non-nucleophilic base in an inert solvent.

10. The process of claim 1, wherein (b) is carried out in the presence of a co-catalyst.

11. The process of claim 10, wherein the co-catalyst is a copper salt or a cerium salt.

12. The process of claim 1, wherein (b) carried out in the presence of an oxidant.

13. The process of claim 12, wherein the oxidant is selected $O_2$ gas, an oxidant, and an air atmosphere.

14. The process of claim 1, wherein (b) is carried out in aqueous solutions or in an inert solvent or a mixture of solvents selected from dioxane, toluene, benzene, DMF, $C_{1-6}$alkylOH, acetonitrile, diethylcarbonate, ionic liquids, water, dilute aqueous acid and dilute aqueous base.

15. The process of claim 1, wherein the reducing agent in (c) is a metal hydride reducing agent.

16. The process of claim 15, wherein the metal hydride reducing agent is lithium aluminum hydride or sodium bis(2-methoxyethoxy)aluminum hydride.

* * * * *